(12) United States Patent
Van Oort et al.

(10) Patent No.: US 8,540,642 B2
(45) Date of Patent: Sep. 24, 2013

(54) IMPLANTABLE MEDICAL DEVICE AND METHOD FOR PHYSIOLOGICAL EVENT MONITORING

(75) Inventors: Geeske Van Oort, Velp (NL); Willem Boute, Brummen (NL); Gustaaf A. P. Stoop, Dieren (NL)

(73) Assignee: Medtronic, Inc., Minneapolis, MN (US)

( * ) Notice: Subject to any disclaimer, the term of this patent is extended or adjusted under 35 U.S.C. 154(b) by 2088 days.

(21) Appl. No.: 11/669,345

(22) Filed: Jan. 31, 2007

(65) Prior Publication Data

US 2008/0183085 A1    Jul. 31, 2008

(51) Int. Cl.
*A61B 5/04*    (2006.01)

(52) U.S. Cl.
USPC .......................... 600/508; 600/509

(58) Field of Classification Search
USPC ........................................ 600/508
See application file for complete search history.

(56) References Cited

U.S. PATENT DOCUMENTS

| | | |
|---|---|---|
| 4,374,382 A | 2/1983 | Markowitz |
| 5,379,776 A | 1/1995 | Murphy et al. |
| 5,513,645 A | 5/1996 | Jacobson et al. |
| 5,545,186 A | 8/1996 | Olson |
| 5,622,178 A | 4/1997 | Gilham |
| 5,782,876 A | 7/1998 | Flammang |
| 5,944,745 A | 8/1999 | Rueter |
| 5,987,352 A | 11/1999 | Klein et al. |
| 6,134,474 A | 10/2000 | Fischell et al. |
| 6,230,055 B1 * | 5/2001 | Sun et al. ........................... 607/5 |
| 6,250,309 B1 | 6/2001 | Krichen et al. |
| 6,393,316 B1 | 5/2002 | Gillberg |
| 6,418,346 B1 | 7/2002 | Nelson et al. |
| 6,442,433 B1 | 8/2002 | Linberg |
| 6,480,745 B2 | 11/2002 | Nelson et al. |
| 6,522,915 B1 | 2/2003 | Ceballos et al. |
| 6,574,511 B2 | 6/2003 | Lee |
| 6,595,927 B2 | 7/2003 | Pitts-Crick et al. |
| 6,599,250 B2 | 7/2003 | Webb et al. |
| 6,671,548 B1 * | 12/2003 | Mouchawar et al. ........... 607/14 |
| 6,823,210 B2 | 11/2004 | Eberle et al. |
| 6,865,419 B2 | 3/2005 | Mulligan et al. |
| 6,931,272 B2 | 8/2005 | Burnes |
| 7,062,314 B2 | 6/2006 | Zhu et al. |
| 7,130,678 B2 | 10/2006 | Ritscher et al. |
| 7,597,667 B2 * | 10/2009 | Hung ............................ 600/508 |
| 2003/0191404 A1 | 10/2003 | Klein |
| 2004/0092836 A1 | 5/2004 | Ritscher |
| 2004/0116972 A1 * | 6/2004 | Marcovecchio ................ 607/14 |
| 2004/0220629 A1 * | 11/2004 | Kamath et al. ..................... 607/6 |
| 2008/0058651 A1 * | 3/2008 | Shen et al. ..................... 600/481 |

OTHER PUBLICATIONS

International Search Report, PCT/US2008/051798, Jun. 24, 2008, 5 Pages.

* cited by examiner

*Primary Examiner* — Carl H Layno
*Assistant Examiner* — Paula J Stice
(74) *Attorney, Agent, or Firm* — Reed A. Duthler; Stephen W. Bauer

(57) ABSTRACT

An implantable medical device uses a method for dynamically managing physiological signal monitoring. A physiological signal is sensed for detecting physiological events in response a first threshold. A determination is made whether a second threshold has been met in response to detecting physiological events. If the second threshold has been met, detailed monitoring of the physiological events is enabled.

39 Claims, 7 Drawing Sheets

IMPLANTABLE MEDICAL DEVICE AND METHOD FOR PHYSIOLOGICAL EVENT MONITORING

TECHNICAL FIELD

The invention relates generally to implantable medical devices and, in particular, to an automatically adaptive method for managing physiological event monitoring.

BACKGROUND

Numerous implantable medical devices (IMDs) are configured for monitoring and storing physiological data for use in diagnosing a patient condition or managing medical therapies. Such devices include implantable cardiac pacemakers, implantable cardioverter defibrillators (ICDs), hemodynamic monitors, subcutaneous ECG monitors, neural stimulators, and the like. An IMD may be capable of detecting numerous types of physiological events based on sensed signals but generally has limited memory capacity due to physical size restraints for storing data relating to detected physiological events. Detection of a physiological event, such as an arrhythmia, may trigger storage of physiological signal data in an IMD. When the memory available for physiological data storage is full, previously stored event episodes may be overwritten with newer events, resulting in a loss of some data.

Older data that is overwritten may correspond to severe or highly clinically significant data. To address this potential loss of valuable data, methods have been proposed for prioritizing data that is stored such that older data is overwritten only when new data is determined to be higher priority data. However, a limitation remains in that a clinician may be unaware what types of physiological events a patient may be experiencing and may therefore not program an implanted device to monitor and store data relating to physiological events that might be important in properly diagnosing and treating the patient. The IMD may store physiological event data corresponding to one type of event while other physiological events go unnoticed or remain poorly documented.

DETAILED DESCRIPTION

Figure 1:
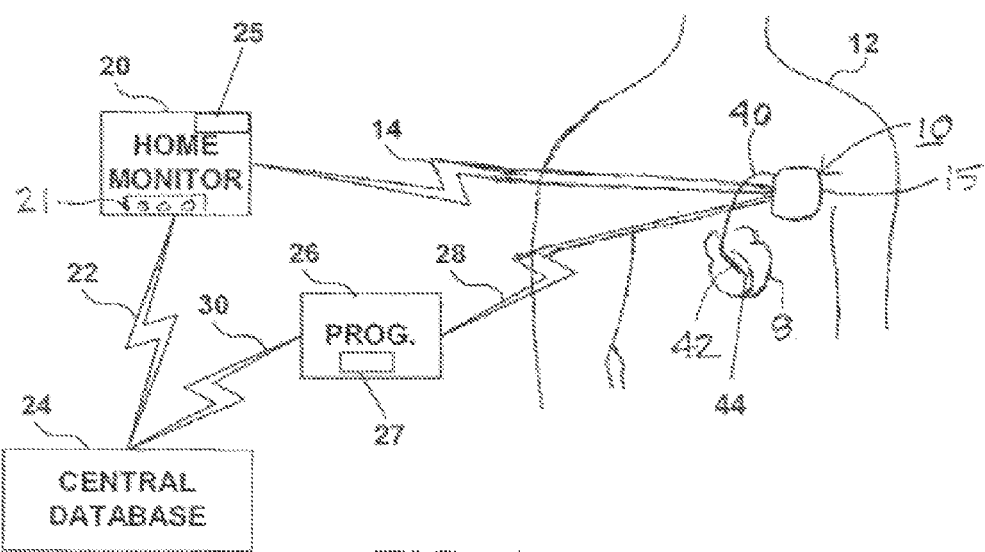
FIG. 1 is a schematic illustration an implantable medical device (IMD) system.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 illustrates an implantable medical device (IMD) system. IMD 10 is shown implanted in a patient 12. The simplified illustration of IMD 10 may represent a variety of IMDs such as a cardiac pacemaker, implantable cardioverter defibrillator, hemodynamic monitor, ECG recorder, or a drug delivery device. In alternative embodiments, an IMD may be implemented as an insulin monitor or pump, or a neuro stimulator. IMD 10 may be coupled to one or more fluid delivery catheters or electrical leads 40. Lead 40 is used for carrying electrodes or physiological sensors used for monitoring one or more physiological signals and delivering electrical stimulation therapies to the patient's heart 8. The IMD 10 may also be embodied with one or more subcutaneous leads for carrying one or more electrodes or other sensors. Furthermore, the IMD 10 may communicate via telemetry within the body of patient 12 with remotely placed sensors. IMD 10 may alternatively be embodied as a leadless device wherein sensors or electrodes are incorporated in or on the housing of IMD 10. Examples of subcutaneous monitoring devices are generally disclosed in U.S. Pat. No. 6,522,915 issued to Ceballos et al., and U.S. Pat. No. 5,987,352 issued to Klein et al, both of which patents are incorporated herein by reference in their entirety.

Lead 40 is a ventricular lead including a coil electrode 42. Coil electrode 42 may be used in conjunction with IMD housing 15 for delivering cardioversion/defibrillation shocks to a patient. Lead 40 may also be provided with a tip electrode and a ring electrode for sensing ventricular signals and delivering cardiac pacing pulses. In one embodiment of the invention, coil electrode 42 is used in conjunction with IMD housing 15 to measure thoracic impedance for thoracic fluid monitoring. In patients suffering from congestive heart failure, an increase in pulmonary fluid congestion will result in a decrease in thoracic impedance. Monitoring of thoracic impedance over time allows a trend of worsening or improving edema to be tracked. Lead 40 is shown positioned in the right ventricle, however a ventricular lead may alternatively be positioned in operative relation to the left ventricle, for example in a cardiac vein via the coronary sinus.

In the embodiment shown, lead 40 further includes a blood pressure sensor 44. In other embodiments, lead 40 or other additional leads may be provided including other physiological sensors, blood chemistry sensors, temperature sensors, oxygen sensors, flow sensors, wall motion sensors or the like. Furthermore, while IMD 10 is shown as a cardiac device coupled to the patient's heart 8 via lead 40, various embodiments of the invention may include other types of implantable medical devices that are enabled for monitoring a physiological signal for detecting a condition or event associated with a change in the monitored signal or a parameter derived therefrom.

IMD 10 is provided with an antenna and associated circuitry, as will be described below, for establishing a communication link 14 with external telemetry circuitry included in home monitor 20 and/or a communication link 28 with external telemetry circuitry 27 included in physician programmer 26. Home monitor 20 may include a user interface 21 that allows patient 12 or other caregiver to transmit commands or signals to IMD 10 using home monitor 20. Home monitor 20 may be configured to receive data from IMD 10 for transmission to a central database 24 to enable remote monitoring of patient 12. In some embodiments, home monitor 20 may be selectively enabled to program an operating mode or control parameters used by IMD 10. Home monitor 20 may be embodied as a bedside or table top unit, a handheld unit or a wearable device.

IMD 10 is further enabled for bidirectional communication with a physician programmer 26 via telemetry link 28. Physician programmer 26 is generally located in a health care facility, such as a clinic or hospital, for use by medical personnel and is typically enabled for full programming and interrogation functionality.

Home monitor 20 and/or programmer 26 may optionally be adapted to communicate with a central database 24 to allow transfer of data received from IMD 10 to the central database 24. A central database may be an Internet-based or other networked database used for remote patient monitoring. Home monitor 20 may transfer data via a communication link 22, which may be established via the Internet, a local area network, a wide area network, a telecommunications network or other appropriate communications network and may be a wireless communication link. Likewise, programmer 26 may receive data from IMD 10 and transfer the data to central database 24 using a communication link 30. Examples of remote monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

Figure 2:
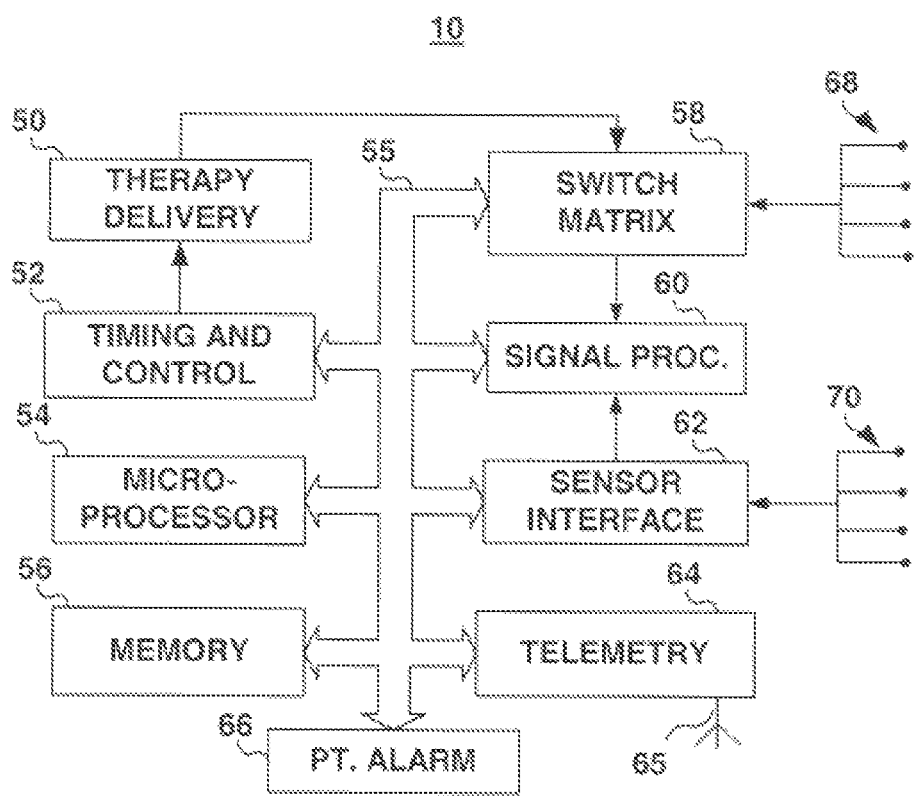
FIG. 2 is a functional block diagram of an IMD, such as the IMD shown in FIG. 1.

FIG. 2 is a functional block diagram of an IMD, such as IMD 10 shown in FIG. 1. IMD 10 generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may be lead-based electrodes, leadless electrodes incorporated on IMD 10, and/or the IMD housing configured for use as a can or case electrode. Electrodes 68 may also be used for sensing electrical signals within the body, such as cardiac signals, or for measuring impedance, such as thoracic impedance for fluid monitoring as described above. Cardiac electrical signals are sensed using any of electrodes 68 for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias, detecting ischemia, detecting changes heart rate variability, etc. Electrodes 68 may be used for measuring impedance signals for monitoring edema, respiration or heart chamber volume. Any of these signals may be used to detect a physiological event. Impedance signals can also be used for monitoring lead performance and detecting lead-related problems.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions according to defined detection thresholds. For example, IMD 10 may monitor thoracic impedance, heart wall motion, blood pressure, blood chemistry, respiration, or patient activity to acquire diagnostic data. Sensed physiological signals may also be used for sensing the need for delivering a therapy under control of the operating system.

As will be described in detail herein, signals from sensors 70 and signals from electrodes 68 are used by microprocessor 54 for generically detecting events corresponding to a number of event categories such as atrial arrhythmias, ventricular arrhythmias, heart failure conditions, or the like, without discriminating between specific types of events falling into a particular event category. Generic detection of events is based on a generic detection threshold. Upon meeting a trigger threshold defined for enabling specific or detailed monitoring of an event category, the microprocessor 54 uses the sensed signals for specifically detecting events within an event category.

The operating system includes associated memory 56 for storing operating commands and data for controlling device operation and for later retrieval of data stored to diagnose device function or patient condition. A portion of memory 56 is allocated for storing data compiled from sensed physiological signals and data relating to device operating history for telemetry out on receipt of a retrieval or interrogation instruction. IMD 10 is configured to monitor numerous physiological signals or parameters and detect a variety of physiological events therefrom. A physiological event detection is typically logged in memory by storing the date, time, event type, and possibly other parametric data such as an event duration or other data derived from the physiological signal used for detecting the event such as a heart rate, a maximum, minimum or average parameter value, or the like.

Detection of a physiological event may further trigger storage of more detailed data such as a snapshot of the physiological signal at the time of the event detection. A "snapshot" of the physiological signal refers to a continuous stream of the sampled physiological signal over an interval of time including the time of the event detection. Marker channel data may also be stored in response to an event detection. Acquisition of marker channel data is generally described in U.S. Pat. No. 4,374,382 to Markowitz, hereby incorporated herein by reference in its entirety. Triggered storage of such detailed data requires greater memory capacity than storage of parametric event data. Triggered data storage of physiological events is generally described in the above-incorporated Klein patent. As the monitoring capabilities of IMD 10 increase, available memory for triggered storage of detailed physiological data becomes limited. Methods are provided herein for dynamically managing physiological signal monitoring and data storage in order to provide a physician with the most important data for diagnostic and disease management purposes. As will be described in detail herein, detailed physiological data corresponding to detected physiological events will be stored when a trigger threshold is met corresponding to a particular category of physiological events.

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit. IMD 10 may be equipped with patient alarm circuitry 66 for generating audible tones, a perceptible vibration, muscle stimulation or other sensory stimulation for notifying the patient that an alarm condition has been detected by IMD 10. An alarm condition may be related to detected physiological events. The patient may respond to the alarm according to physician instructions. In alternative embodiments, a patient alarm may be incorporated in home monitor 20 (shown in FIG. 1) responsive to signals received from the IMD 10. Alarm signals generated by the home monitor 20 can be transmitted to the central database 24 or other communication devices for notifying the patient and/or medical personnel of a medical condition.

Figure 3:
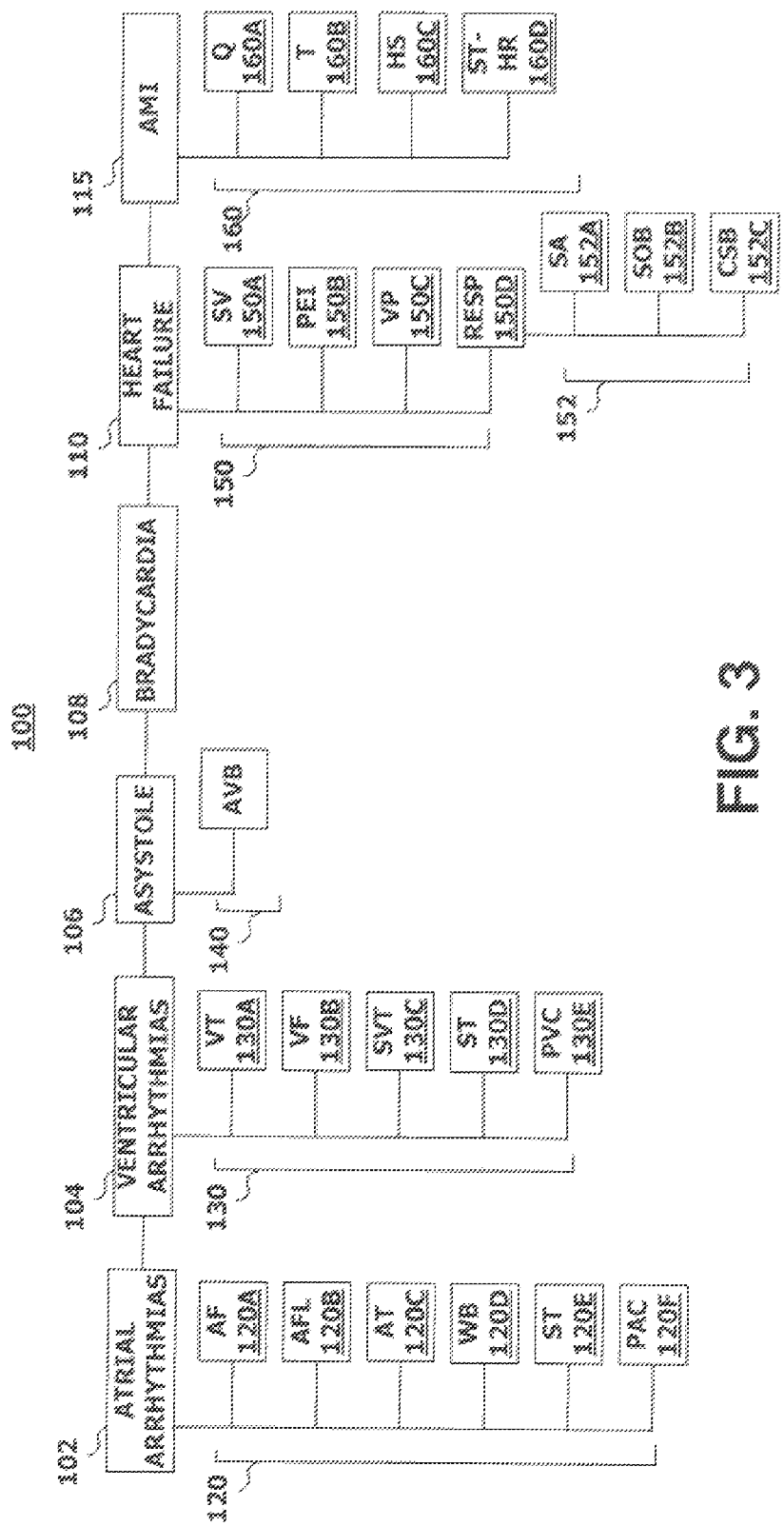
FIG. 3 is a schematic diagram of multiple event categories that may be monitored by an IMD.

FIG. 3 is a schematic diagram of multiple event categories that may be monitored by an IMD. In one embodiment, the IMD is embodied as a cardiac monitoring device capable of generically monitoring multiple cardiac event categories including atrial arrhythmias 102, ventricular arrhythmias 104, asystole 106, bradycardia 108, heart failure 110 and acute myocardial infarction (AMI) 115. The IMD is further capable of specifically monitoring event subcategories 120, 130, 140, 150 and 160 within at least some of the event categories 102, 104, 106, 110 and 115. For example, in specifically detecting events falling into the atrial arrhythmia category 102, the IMD may be capable of discriminating multiple atrial arrhythmia event subcategories 120 including atrial fibrillation (AF) 120A, atrial flutter (AFL) 120B, Wenckebach rhythms (WB) 120D, atrial tachycardia (AT) 120C, sinus tachycardia (ST) 120E, and premature atrial contractions (PAC) 120F.

In specifically detecting events falling into the generic ventricular arrhythmia category 104, the IMD may be capable of discriminating between ventricular tachycardia (VT) 130A (which may further include discrimination between fast and slow VT), ventricular fibrillation (VF) 130B, supraventricular tachycardia (SVT) 130C, sinus tachycardia (ST) 130D, and premature ventricular contractions (PVC) 130E. If asystole is detected, the IMD may be capable of determining if the asystole is associated with AV block (AVB) 140.

Generic heart failure monitoring 110 may include monitoring one or more physiological signals corresponding to hemodynamic measurements or detecting heart failure symptoms. In one embodiment, the thoracic impedance is monitored for detecting a generic heart failure event 110. As a heart failure condition worsens, an increase in thoracic fluid level (pulmonary edema) results in a corresponding decrease in thoracic impedance. The increase in thoracic fluid level may be associated with other worsening heart failure conditions or symptoms. Reference is made, for example, to U.S. Pat. No. 6,595,927 to Pitts-Crick et al., hereby incorporated herein by reference. As such, additional detailed monitoring of specific heart failure conditions or symptoms may be performed including measuring stroke volume 150A, measuring pre-ejection interval (PEI) 150B, measuring ventricular pressure 150C, and monitoring respiration 150D. The subcategory of respiration measurements 150D may be further discriminated between specific breathing disorders associated with heart failure such as sleep apnea (SA) 152A, shortness of breath (SOB) 152B, and Cheyne-Stokes breathing (CSB) 152C. As such, it is recognized that any of the subcategories 120, 130, 140, 150 and 160 may include additional layers of subcategories, such as the respiration event subcategories 152.

Generic acute myocardial infarction monitoring 115 may be performed by detecting changes in the ST segments of sensed ECG/EGM signals. Specific monitoring of acute myocardial infarct subcategories 160 may include monitoring Q-wave morphology (Q) 160A, T-wave morphology (T) 160B, heart sounds (particularly S3 and S4) (HS) 160C, and ST-heart rate hysteresis loops (ST-HR) 160D.

Initially, a physician may be unaware of what types of cardiac events a patient may be experiencing. Since IMD processing power and memory capacity are limited, it is desirable to monitor and store data that has the greatest clinical relevance to diagnosing and treating the patient. Without knowing what events the patient might be experiencing, the physician may program an IMD to monitor and store some specific types of cardiac events without enabling the IMD to store other types of cardiac events. As such, the physician may be unaware that the other events are occurring or may not have enough detailed data available regarding such events to make an informed diagnosis.

In order to determine which events are occurring in an individual patient and store the most clinically relevant of these events, a dynamic physiological monitoring management method is implemented that initially allows the IMD to generically monitor for cardiac events corresponding to each of the broader cardiac event categories 102, 104, 106, 108, 110, and 115 without performing specific monitoring of subcategory events. For example, and as will be described in greater detail below, the IMD may be enabled to generically monitor for atrial arrhythmias 102 without discriminating between the specific types of atrial arrhythmias 120. The IMD may be enabled to generically monitor for ventricular arrhythmias 104 without being enabled to discriminate between the specific types of ventricular arrhythmias 130. Generally, ventricular arrhythmias are more serious in nature and, as such, the IMD may be enabled to at least discriminate between the most serious forms of ventricular arrhythmias, e.g., VF and VT, without more detailed detection or discrimination of other specific event types (fast VT vs. slow VT, PVCs, SVT etc.). The IMD may be enabled to generically monitor for heart failure by monitoring changes in thoracic impedance without being enabled to perform more detailed monitoring of other heart failure conditions or symptoms.

As used herein, "generic monitoring" refers to monitoring for events falling within a defined event category. The event category includes a number of specific types of events, or subcategories as described above, which can all be grouped under the broader event category definition. Generic monitoring is performed without detecting the specific subcategory events. "Detailed monitoring" of an event category refers to monitoring and detecting the specific subcategory events and/or triggering the storage of detailed physiological data in response to an event detection. The detection of specific subcategory events may involve the use of discrimination or classification algorithms for discriminating between subcategory events, e.g. discriminating between different types of arrhythmias. The detection of specific subcategory events may additionally or alternatively involve monitoring of additional physiological signals or signal parameters, other than the signal(s) or signal parameters used for generically detecting category events. Triggered data storage refers to the storage of physiological signal snapshots, marker channel data, or other detailed physiological data relating to an event detection that requires relatively more memory capacity than parametric-type data storage.

As will be further described below, the IMD is initially enabled to perform generic monitoring of the event categories 102, 104, 106, 108, 110 and 115 without performing detailed monitoring. A trigger threshold is defined for each of the event categories 102 through 115, which when met enables detailed monitoring of the event category. The trigger threshold is generally a measure of the severity of the generic event detections corresponding to a particular event category.

It is recognized that the physician may initially configure the IMD to perform detailed monitoring of any of the generic event categories 102, 104, 106, 108, 110 and 115 when the physician is aware of a particular patient condition. However, by configuring the IMD to also generically monitor for other event categories, generic events corresponding to other categories may be detected and if the severity of the generic events reaches the trigger threshold, detailed monitoring of those other event categories becomes enabled automatically.

Since a physician may initially be unaware of which cardiac event categories are the most important to monitor in a particular patient, the physician need not select which event types will trigger detailed data storage. Instead, the IMD is configured to generically detect events occurring in each of the event categories 102, 104, 106, 108, 110 and 115 and upon determining that the trigger threshold corresponding to a particular event category has been met, detailed monitoring is enabled. In past practice, detection of a physiological event according to an event detection threshold also triggered storage of physiological data corresponding to that event. In accordance with various embodiments of the invention, a trigger threshold for a particular event category is defined separately from an event detection threshold such that event detection alone does not trigger data storage unless the trigger threshold has also been met.

Generic events are detected according to a generic event detection threshold and such detections may be logged in memory with other parametric data, without storing detailed physiological data or performing specific subcategory event monitoring. If the trigger threshold is met for a particular event category in response to generic event detection(s), detailed monitoring of the event category is enabled to allow specific subcategory event detection and triggered storage of detailed physiological data in response to an event detection. In some embodiments, the programmer may be configured to automatically suggest a certain combination of generic and specific event monitoring according to the primary indication for implanting the IMD. In this way, some event subcategories are immediately enabled for detailed monitoring without having to wait until a trigger threshold is met.

For example, the atrial arrhythmia category 102 may be monitored according to a generic atrial arrhythmia (AA) detection threshold. In one embodiment, a generic atrial arrhythmia detection threshold is defined as a function of ventricular cycle length variability. If the generic AA detection threshold is crossed, an atrial arrhythmia is detected without further analysis of the ventricular cycle length variability for discriminating between specific subcategory events, i.e. AF, AFL, etc. In another embodiment, generic AA event monitoring is based on atrial rate (P-P intervals) with a generic AA event being detected when the atrial rate exceed a generic AA detection threshold, e.g. 120 beats per minute. A generic detection threshold may include one or more criteria. For example, a generic AA detection threshold based on atrial rate may include a rate threshold criteria, e.g. 120 beats per minute, and a stability threshold criteria, e.g. an abrupt change in rate of more than 15 beats/min). If both the rate threshold and stability threshold conditions are met then a generic atrial arrhythmia event is detected.

Another threshold, referred to as the "trigger threshold" herein, is set as a function of a metric of the AA event category. An event category metric is generally a measure of the severity of detected generic events. In one embodiment, an AA event metric is the summed durations of all generically detected atrial arrhythmia episodes occurring over a predetermined time interval, also referred to herein as the "atrial arrhythmia burden." An atrial arrhythmia burden may be measured, for example, as the total duration of generic AA episodes occurring over a 24 hour period. Alternatively the AA event category metric may be defined as a frequency of generic atrial arrhythmia detections. Each time an atrial arrhythmia is detected, the AA event category metric is computed and a determination is made if the trigger threshold has been reached. If the atrial arrhythmia burden or the frequency of atrial arrhythmia detections reaches the trigger threshold, detailed monitoring of atrial arrhythmias is enabled. Detailed monitoring includes discrimination of specific atrial arrhythmia events and triggered data storage in response to atrial arrhythmia detections. Triggered data storage includes an EGM/ECG snapshot and marker channel recordings as well as other parametric data pertaining to the detected event.

Figure 4:
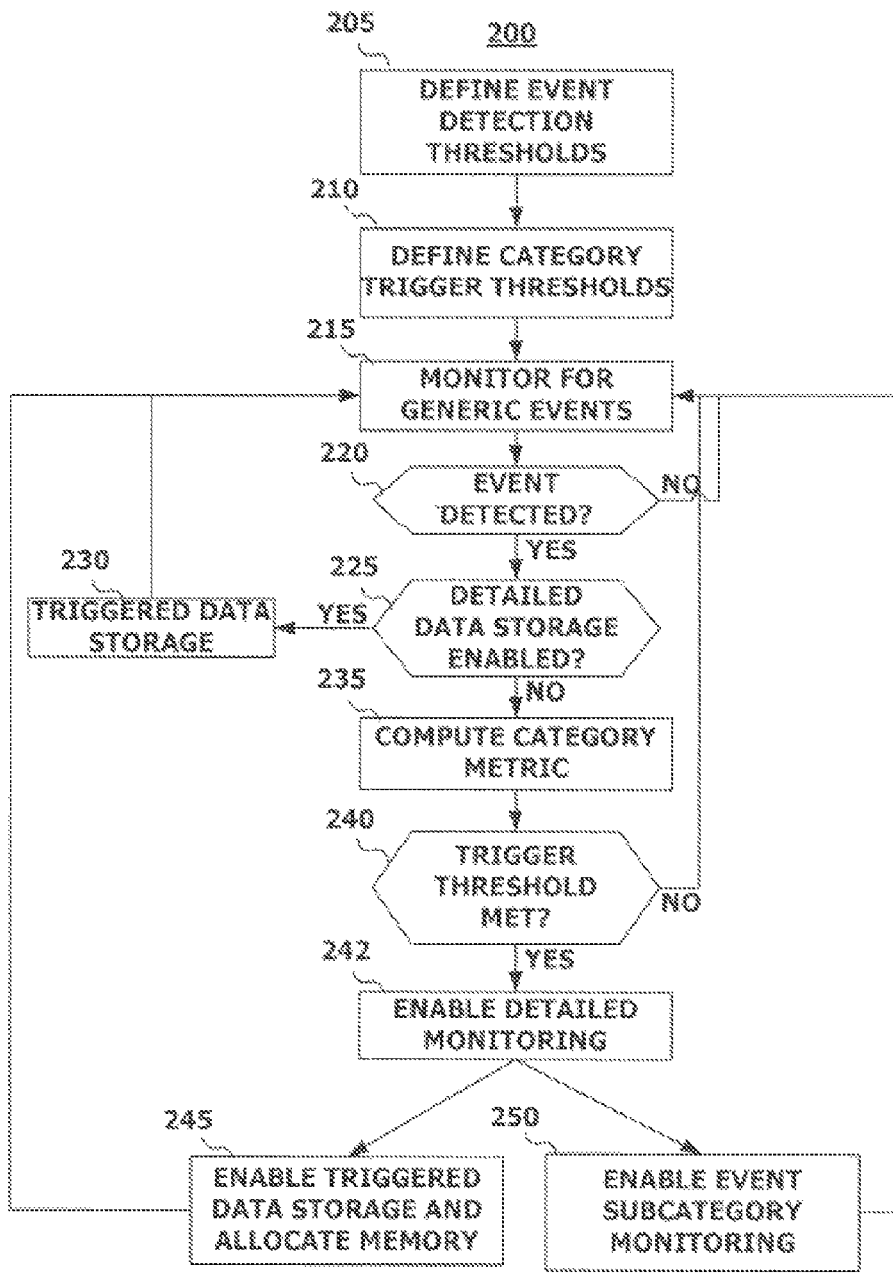
FIG. 4 is a flow chart of one method for dynamically managing physiological event monitoring and data storage according to one embodiment of the invention.

FIG. 4 is a flow chart of one method for dynamically managing physiological event monitoring and data storage according to one embodiment of the invention. Flow chart 200 is intended to illustrate the functional operation of the device, and should not be construed as reflective of a specific form of software or hardware necessary to practice the invention. It is believed that the particular form of software will be determined primarily by the particular system architecture employed in the device and by the particular event detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 205, physiological event detection thresholds are defined and stored for use by the IMD in detecting events using physiological signals sensed by the IMD. Event detection thresholds include both generic detection thresholds corresponding to generic monitoring of each event category and specific detection thresholds corresponding to detailed monitoring of each event subcategory of each event category. Detection thresholds are generally defined as a function of one or more physiological signal parameters. For example, a generic ventricular arrhythmia detection threshold may include an arrhythmia detection interval and a minimum number of arrhythmia intervals required to detect a generic ventricular arrhythmia using a sensed EGM/ECG signal. An generic atrial arrhythmia detection threshold may be defined as a function of a ventricular cycle length irregularity metric derived from a ventricular EGM/ECG signal.

Specific detection thresholds may be defined as functions of additional signals or signal parameters. For example, specific AA detection thresholds may be defined as functions of additional metrics of ventricular cycle length irregularity for discriminating between specific types of atrial arrhythmias, i.e., AF, AFL, etc. Reference is made to U.S. Pat. No. 7,031, 765 to Ritscher et al., and U.S. Pat. Application Publication No. 2004/0092836 to Ritscher et al., both of which are incorporated herein by reference in their entirety. Likewise, specific detection thresholds are defined for discriminating between slow VT, fast VT, VF, SVT etc., which may be defined by conditions relating to P-wave and R-wave event patterns and signal morphology in addition to ventricular rate conditions. Reference is made, for example, to U.S. Pat. No. 5,545,186 to Olson et al. and U.S. Pat. No. 6,393,316 to Gillberg et al., both of which patents are incorporated herein by reference. The specific thresholds defined for detailed monitoring of event subcategories may be based on the same or different physiological signal parameters as the generic detection threshold defined for the event category.

At block 210, trigger thresholds are defined for each of the event categories. Trigger thresholds may relate to the severity, frequency or duration of generic events detected for a particular event category. For example the trigger threshold for atrial or ventricular arrhythmias may relate to a maximum arrhythmia rate, maximum arrhythmia episode duration, an arrhythmia burden, arrhythmia frequency or other metric of the severity of the detected generic arrhythmia events. A trigger threshold for heart failure may be a defined change in thoracic impedance. Unlike the generic or specific event detection thresholds used for detecting events from a physiological signal(s), the trigger threshold is used to determine when one or more events that have already been detected reach a level considered to be clinically significant and therefore warrant detailed monitoring of the event category.

At block 215, the IMD monitors for physiological events. The IMD is initially enabled to perform generic monitoring of events falling into the each event category, without performing detailed monitoring for specific detection of subcategory events. If a generic event is detected, as determined at decision block 220, the IMD determines if triggered data storage is enabled for the detected event at block 220. Triggered data storage is generally not enabled until the previously defined trigger threshold has been met for the associated event category. If triggered data storage is not enabled, the generic event detection may still be logged in memory. Logging a generic event detection in memory when triggered data storage is not enabled may include storing parametric data such as the time and date of the detection, the generic event category and other parameter values derived from the sensed signal such as an event episode duration, an atrial or ventricular rate, a ventricular cycle length irregularity metric, a daily mean thoracic impedance measurement, or other signal-derived parameter used in making the generic event detection.

If triggered data storage is not yet enabled, as determined at block 225, a metric of the event category is computed at block 225 in response to the event detection. A category metric is a measure of the frequency, duration or other severity marker of the detected generic events associated with a particular event category. If the category metric meets the previously defined trigger threshold, as determined at decision block 240, detailed monitoring is enabled at block 242 for the corresponding event category. Detailed monitoring includes triggered data storage 245 and/or specific subcategory event monitoring 250. Once the trigger threshold has been met, the current event and/or all future detected events corresponding to the event category will trigger detailed data storage at block 230.

Specific event subcategory monitoring 250 relates to discrimination/detection of event subcategories, which may include monitoring of additional physiological signals or signal parameters. As described above, the IMD is initially enabled for generically monitoring events falling into event categories without performing more detailed discrimination or classification of specific event types. At block 250, discrimination algorithms may be enabled, for example, for discriminating between different types of atrial arrhythmias and ventricular arrhythmias. The IMD is thus enabled for detecting specific event subcategories as shown in FIG. 3. Detailed monitoring enabled at block 250 may additionally or alternatively include monitoring of other physiological signals or parameters different than the signal or parameter used for generic event detection. For example, if generic heart failure events are detected based on a measurement of thoracic impedance, specific subcategory event monitoring may include monitoring of a pressure signal, accelerometer signal, blood chemistry signal, or other physiological signals that change with a worsening of heart failure.

After enabling detailed monitoring of an event category, method 200 returns to block 215 to continue monitoring for physiological events. Generic monitoring for category events is performed for those categories which have not yet met an associated trigger threshold. Detailed monitoring is performed for the categories which have met an associated trigger threshold.

Depending on the particular application, the IMD may optionally be programmed by the physician to initially perform detailed monitoring of a particular category. For example, if the IMD is configured to monitor ventricular arrhythmias, detailed monitoring including discrimination between specific ventricular arrhythmias (e.g., slow VT, fast VT, VF, sinus VT, SVT, etc.) may be enabled by the physician. It is recognized that an IMD may be configured to monitor for events falling into various event categories, with some event categories initially programmed for detailed event monitoring and other event categories initially disabled for detailed event monitoring (generic monitoring only). In some embodiments, the physician may have the option to initialize the IMD to perform triggered data storage for one or more event categories or event subcategories before a trigger threshold is met. For example, if the IMD is enabled for monitoring ventricular arrhythmias, the physician may be interested in triggering detailed data storage for all generic or specific ventricular arrhythmia detections due to the seriousness of such arrhythmias, without waiting for a ventricular arrhythmia trigger threshold to be met. As such, a portion of the IMD memory may be initially allocated for triggered data storage for a particular event category. Other IMD memory may remain unallocated until other trigger thresholds are met for a particular category and triggered data storage is enabled.

Figure 5:
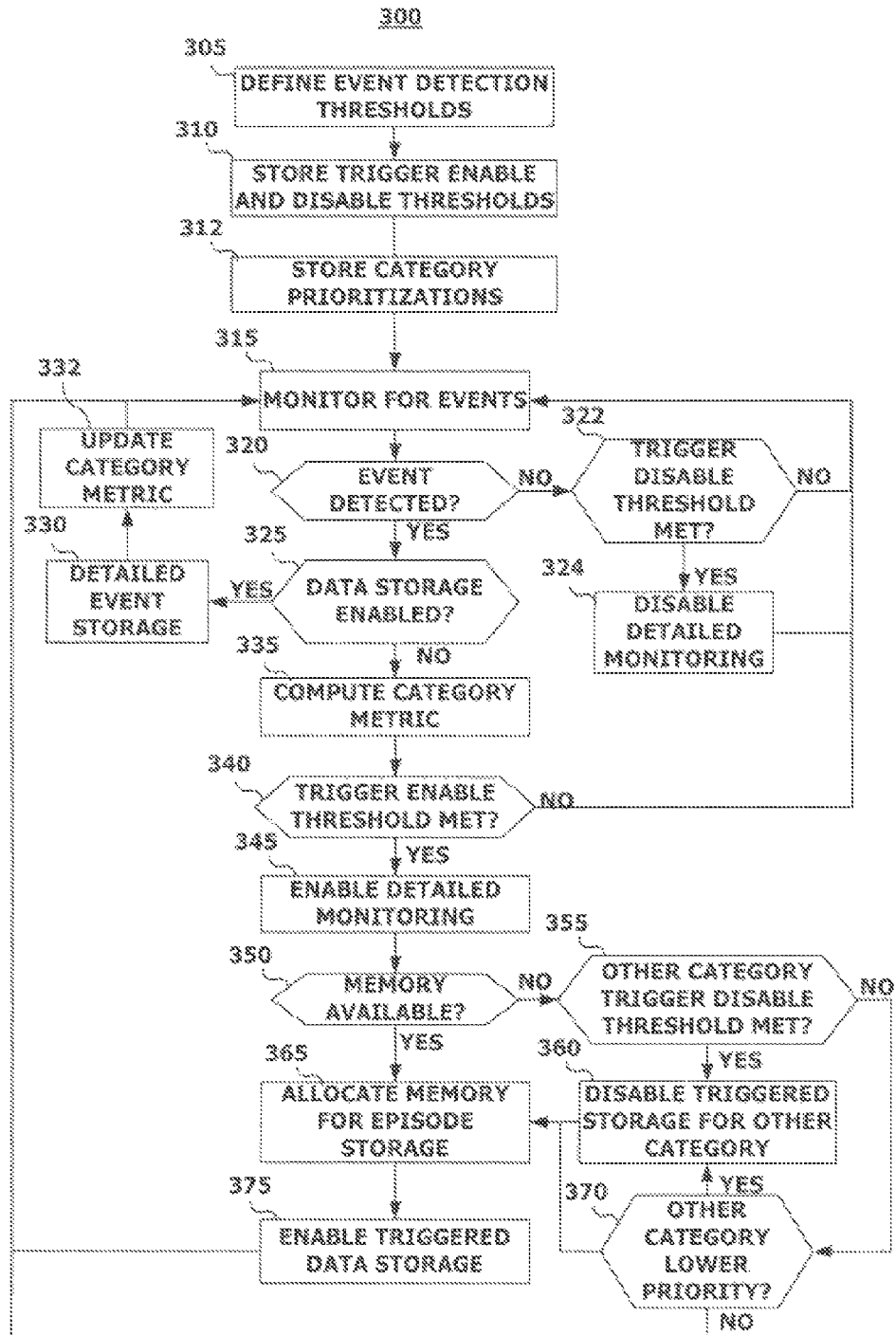
FIG. 5 is a flow chart of an alternative embodiment for dynamically managing physiological event monitoring.

FIG. 5 is a flow chart of an alternative embodiment for dynamically managing physiological event monitoring. In method 200 of FIG. 4, once a trigger threshold is met, detailed monitoring of the associated event category continues until reprogrammed by a clinician. However, events falling into a particular category may subside or become alleviated by delivered therapies such that detailed monitoring of the event category is no longer needed. Furthermore, other event categories may reach an associated trigger threshold and have greater diagnostic or disease management importance than another, previously-enabled category. Method 300 shown in FIG. 5 allows dynamic management of detailed monitoring of event categories according to category metrics measured over time and corresponding trigger thresholds. At block 305, event detection thresholds are defined. Event detection thresholds include generic and specific detection thresholds that will be used generic event detection as well as specific subcategory event detection, respectively.

At block 310, a trigger enable threshold and a trigger disable threshold are defined and stored for each event category monitored by the IMD. A trigger enable threshold is a threshold defined as a function of a category metric, such as a duration, frequency or other severity marker of the event category as described previously. The IMD responds to a trigger enable threshold being met by enabling detailed monitoring of an associated event category. A trigger disable threshold is a threshold that is also defined as a function of the category metric. The trigger disable threshold is generally defined to correspond to a less severe level of the category metric than the trigger enable threshold, though in some embodiments, the trigger enable threshold and the trigger disable threshold may be equal. The IMD responds to a trigger disable threshold being met by disabling detailed monitoring of associated category events.

At block 312, prioritization of event categories is stored. Higher priority event categories generally correspond to events considered to be more clinically significant, debilitating, or life-threatening than other events. For example, ventricular arrhythmia events may be given a priority greater heart failure events and atrial arrhythmia events. Heart failure events may be given a higher priority than atrial arrhythmia events, and so on. Prioritization of event categories may be pre-defined or programmable according to physician preference.

At block 315, event monitoring is performed. Event monitoring may include both generic and specific event monitoring according to the status of each event category. Upon detecting an event at block 320, the IMD determines if detailed event monitoring has been enabled previously. If detailed monitoring is previously enabled, detailed event data is stored at block 330. An associated category metric is updated at block 332. In some embodiments, if the category metric falls below the trigger disable threshold, detailed monitoring of the event category is disabled. Therapies may be delivered by the IMD in response to detected events, resulting in alleviation of the detected events. As a result, detailed monitoring of the detected events may no longer be necessary. As such, the associated category metric may be updated upon each event detection at block 332 after detailed monitoring has been enabled.

If detailed event monitoring is not enabled, the category metric is computed at block 335 in response to the event detection. The category metric is compared to the trigger enable threshold at block 340. If the trigger enable threshold is met, detailed monitoring of the subcategory events is enabled at block 345. Detailed event monitoring may include triggered data storage and/or specific event subcategory monitoring as described previously.

Upon enabling detailed monitoring at block 345, the IMD determines if memory is available to be allocated for storing detailed event data associated with the newly enabled event category at block 350. If memory is available, a portion of memory is allocated to storing event data corresponding to the enabled category at block 365. If memory is not available, other event category metrics are examined at block 355. This examination may include computing an updated metric for some or all of the other event categories. If another category metric is determined to be less than the trigger disable threshold for that category, and that event category is currently enabled for detailed monitoring, the triggered storage of detailed data for that event category is disabled at block 360. Memory allocated for storing data pertaining to this other event category is made available for reallocation to the newly enabled event category at block 365. Detailed monitoring of other event categories may continue when the trigger disable threshold is met as long as memory remains available and no other event category becomes enabled for detailed monitoring requiring a reallocation of memory. However, if memory is not available for a newly enabled event category and another event category metric has met the trigger disable threshold, detailed monitoring is disabled for that event category to allow a reallocation of memory.

If no other event category metrics have met the trigger disable threshold, as determined at block 355, a comparison of event category prioritizations is made at decision block 370. If the newly enabled event category is a higher priority category than another enabled event category, the triggered storage of detailed event data is disabled for the lower priority event category at block 360. Memory is made available for reallocation to the newly enabled event category at block 365. Upon allocating memory for detailed event data storage at block 365, triggered data storage is enabled for the newly enabled event category at block 375. Method 300 then returns to block 315 to continue to monitor for events. The lower priority event category may remain enabled for detailed monitoring in that specific subcategory event detection may continue with parametric data being logged to memory even though detailed data storage is not performed.

If no other enabled event category metric meets the trigger disable threshold and no other enabled event category is a lower priority than the newly enabled event category, memory is not allocated for detailed event storage for the newly enabled event category. Detailed monitoring may still be performed for specifically detecting subcategory events. Logging of parametric data relating to such specific event detections may still occur even when available memory is insufficient for triggered storage of detailed event data.

Periodic examination of event category metrics may be performed as indicated at block 322, even when no events are detected at block 320. For example, an atrial arrhythmia event category metric defined as an atrial arrhythmia burden may be re-determined on a periodic basis. If the atrial arrhythmia metric falls below the trigger disable threshold, as determined at block 322, and if detailed monitoring of atrial arrhythmias had previously been enabled, the detailed monitoring is disabled at block 324. Disabling detailed monitoring of an event category at block 324 may include reallocating memory currently allocated to the disabled event category to other enabled event categories.

Figure 6:
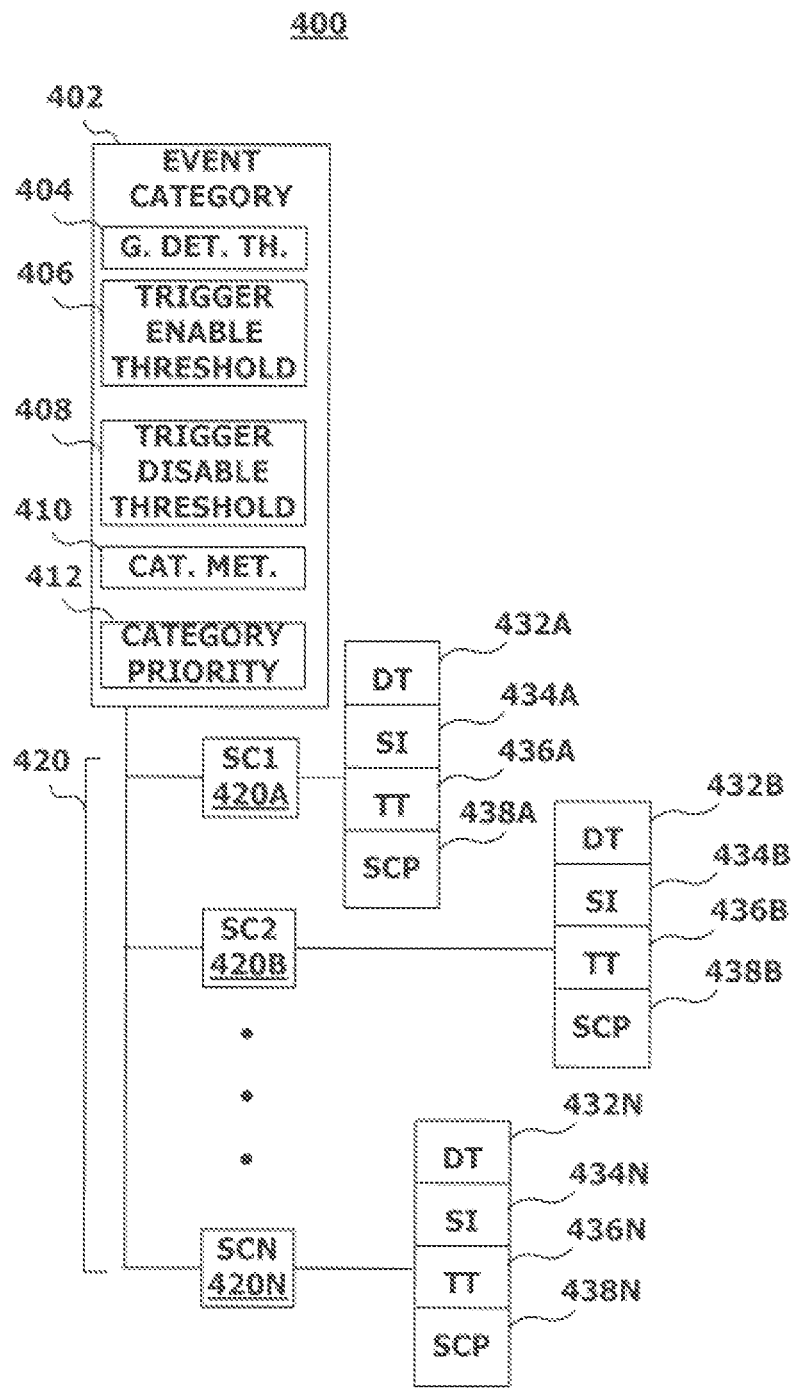
FIG. 6 is a schematic diagram of control parameters that are stored in association with each event category for use in dynamically managing detailed event monitoring according to one embodiment of the invention.

FIG. 6 is a schematic diagram of control parameters that are stored in association with each event category for use in dynamically managing detailed event monitoring according to one embodiment of the invention. Memory may become limited for storing detailed event data after the IMD has been implanted for a period of time or after multiple event categories have been enabled for triggered data storage. As such, in addition to dynamically managing the detailed monitoring of various event categories, prioritization of detailed event data within and between categories is needed to promote storage of the most clinically relevant data while reducing storage of data considered to be less relevant.

Diagram 400 represents the various control parameters that may be defined and stored in association with one event category 402. A generic detection threshold (G. DET. TH.) 404 is defined for generic detection of category events. This generic detection threshold 404 is used detecting category events prior to enabling detailed monitoring of category 402. A trigger enable threshold 406 and optionally a trigger disable threshold 408 are defined as functions of a category metric 410 as described above. The category metric 410 is defined as a measure or index of the severity of generic category events as described above. A category priority 412 is stored indicating the priority of event category 402 relative to other event categories monitored by the IMD.

In one embodiment, a number of control parameters are defined and stored for dynamically managing detailed monitoring of event subcategories 420. Monitoring of event subcategories 420 is enabled in response to the trigger enable threshold 406 being met. As such, a specific detection threshold (DT) 432A, 432B, . . . 432N, is defined for each event subcategory (SC1, SC2, . . . SCN)) 420A, 420B through 420N for use in detecting/discrimination specific subcategory events 420. In addition, a severity index 434A, 434B, . . . 434N, a trigger threshold 436A, 436B, . . . 436N and a subcategory priority 438A, 438B, . . . 438N may be defined for each subcategory 420.

The severity index 434A, 434B, . . . 434N is a measure or index of the severity of a detected subcategory event. The severity index 434A, 434B, . . . 434N allows events falling into the same subcategory to be prioritized against each other based on their relative severity. For example, a ventricular tachycardia may be assigned a severity index as a function of average rate and/or episode duration. When detailed monitoring of ventricular arrhythmias is enabled, the severity index of a detected VT event will be compared to the severity index of previously stored VT events to determine if a less severe VT event has been stored previously. The less severe VT event will be overwritten by the newly detected, more severe VT event when available memory allocated for the VT event subcategory is full.

The trigger threshold 436A, 436B, . . . 436N is defined for enabling detailed monitoring of another layer of subcategory events (not shown in FIG. 6). For example, if heart failure monitoring has been enabled for detailed monitoring and a number or respiration events are detected meeting a subcategory trigger threshold 436A, 436B, . . . 436N, further detailed monitoring of respiration events may be enabled to allow monitoring and discrimination of respiration events such as shortness of breath, sleep apnea, and Cheyne-Stokes breathing. This additional layer of respiration subcategories was previously described in conjunction with FIG. 3. Though not specifically shown in FIG. 6, it is recognized that trigger thresholds 436A, 436B, . . . 436N stored for event subcategories 420 may include both trigger enable thresholds and trigger disable thresholds.

The subcategory priority 438A, 438B, . . . 438N allows a detected subcategory event to be prioritized against previously stored events falling into other subcategories within the same event category 402. If the memory allocated to an event category is full, a detected subcategory event may overwrite a previously stored subcategory event having a lower priority that the detected subcategory.

Figure 7:
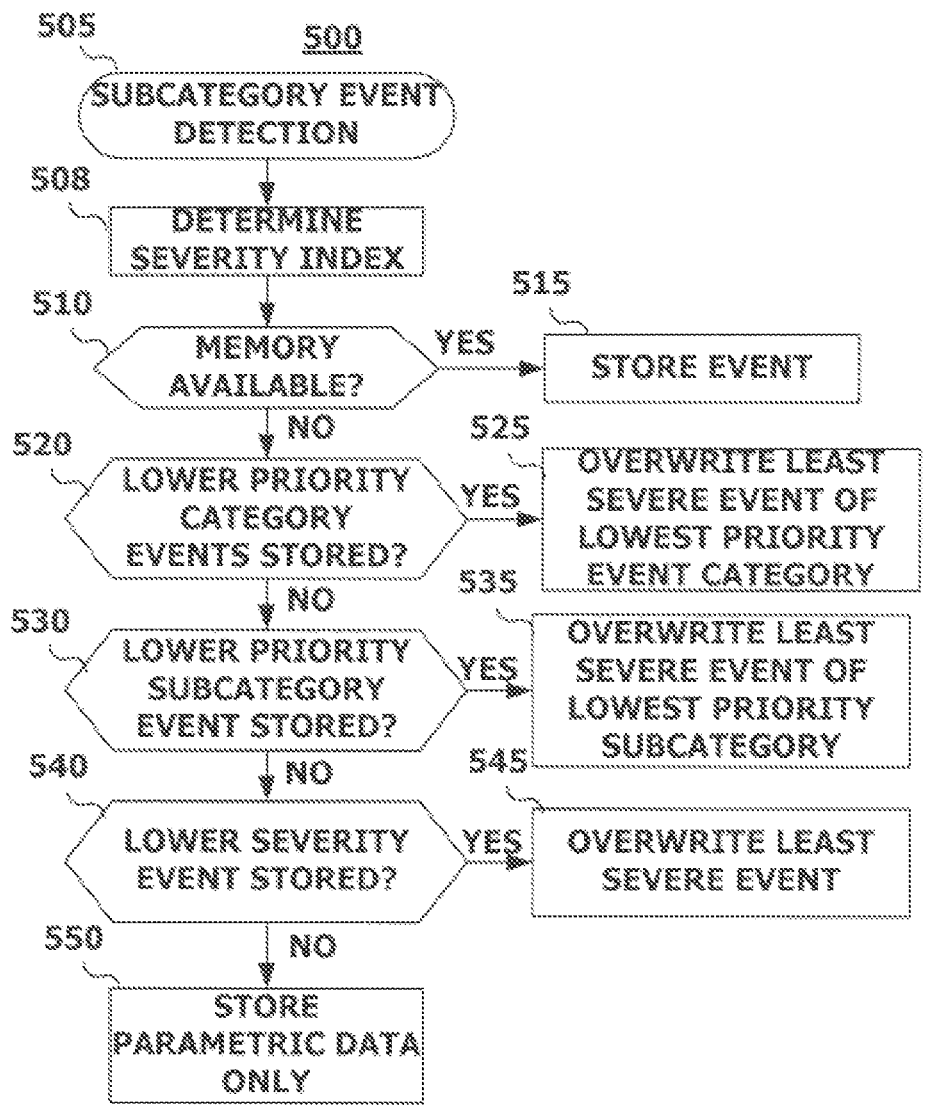
FIG. 7 is a flow chart of one method for prioritizing detailed data storage during dynamically-managed physiological event monitoring.

FIG. 7 is a flow chart of one method 500 for prioritizing detailed data storage during dynamically-managed physiological event monitoring. At block 505, a subcategory event is detected corresponding to a category previously enabled for detailed monitoring as described above. At decision block 510, the IMD determines if memory is available for storage of detailed event data. If memory is available, the detailed physiological data corresponding to the detected event is written to memory at block 515. Detailed data storage may include storage of the severity index.

If memory is not available, the IMD determines if any previously stored events correspond to a lower priority event category at decision block 520. If an event corresponding to a lower priority category has been stored, the least severe event stored for the lowest priority event subcategory within the lowest priority event category is identified at block 525 and overwritten by the current event data.

If no other stored events correspond to a lower priority event category, as determined at block 520, the IMD determines if any other stored events correspond to a lower priority subcategory event within the same event category at block 530. In other words, the IMD determines if any other subcategory events occurring within the same event category of the newly detected event are of a lower priority than the newly detected event subcategory. If another stored event is found to be a lower priority subcategory event, the least severe event stored for the lowest priority subcategory is identified at block 535 and overwritten by the new event data.

If no other stored events are found corresponding to either a lower priority event category or a lower priority event subcategory, the IMD determines if any other stored events corresponding to the same event subcategory of the newly detected event have a lower severity index than the newly detected event at decision block 540. Determining a less severe event may involve computing a severity index for other stored events if the severity index has not been previously stored for each of the other stored events. If a less severe event is found, the least severe event stored for the same subcategory of the newly detected event is identified and overwritten by the new event data at block 545.

If no less severe or lower priority stored events can be identified, detailed data storage for the newly detected event is abandoned. Parametric data for the newly detected event may still be logged to memory at block 550. By maintaining a prioritization of event categories and event subcategories and determining a severity index of individually detected events, event data determined to be relatively more severe or higher priority data is stored by overwriting less severe or lower priority data.

Thus, a system and associated methods for dynamically managing physiological event monitoring have been presented in the foregoing description with reference to specific embodiments. Specific embodiments described herein have related to a cardiac monitoring device configured for monitoring various arrhythmia and heart failure events. It is recognized that other embodiments may be implemented in other types of implantable medical devices configured for monitoring other types of physiological signals and events. It is appreciated that various modifications to the referenced embodiments may be made without departing from the scope of the invention as set forth in the following claims.

The invention claimed is:

1. A method for use in an implantable medical device, comprising:
    storing a first threshold corresponding to detecting a first physiological event;
    sensing a first physiological signal corresponding to the first physiological event;
    detecting a plurality of the first physiological events in response to the first physiological signal and the first threshold;
    storing a second threshold different than the first threshold;
    determining, in response to detecting at least one of the plurality of the first physiological events, if the second threshold has been met; and
    enabling detailed monitoring of next ones of the detected plurality of the first physiological events in response to the second threshold being met.

2. The method of claim 1 wherein the first physiological event corresponds to a first event category comprising a plurality of first physiological event types, and the detailed monitoring comprises monitoring the plurality of the first physiological event types.

3. The method of claim 2 wherein the detailed monitoring comprises storing physiological signal data in memory in response to detecting an event and further comprising;

storing a priority for each of the plurality of first physiological event types, comparing the priority of one of the plurality of the first physiological event types corresponding to the detected event and the priority of an other of the plurality of the first physiological event types, and if the priority of the one of the plurality of the first physiological event types corresponding to the detected event is higher than the priority of the other of the plurality of the first physiological event types, overwriting previously stored physiological signal data corresponding to a previously detected event with physiological signal data corresponding to the detected event, the previously detected event corresponding to the other of the plurality of the first physiological event types.

4. The method of claim 3 wherein the detailed monitoring further comprises:

determining a severity index for the detected event;

comparing the severity index for the detected event to a severity index of a previously stored event of the same event type;

if the severity index for the detected event corresponds to a more severe event than the previously stored event, determining the least severe of a plurality of previously stored events of the same event type; and overwriting the least severe of the plurality of the previously stored events with physiological data corresponding to the detected event.

5. The method of claim 2 wherein monitoring the plurality of the first physiological event types comprises discriminating between the plurality of the first physiological event types in response to the first physiological signal.

6. The method of claim 2 wherein the detailed monitoring further comprises sensing a second physiological signal and wherein monitoring the plurality of the first physiological event types includes detecting at least one of the plurality of the first physiological event types in response to the second physiological signal.

7. The method of claim 2 further comprising:

storing a third threshold corresponding to detecting a second physiological event;

sensing a second physiological signal corresponding to the second physiological event, the second physiological event corresponding to a second event category comprising a plurality of second physiological event types;

detecting a plurality of the second physiological events in response to the second physiological signal and the third threshold;

storing a fourth threshold different than the third threshold;

determining, in response to detecting at least one of the plurality of the second physiological events, if the fourth threshold has been met; and enabling detailed monitoring of next ones of the detected plurality of the second physiological events in response to the fourth threshold being met.

8. The method of claim 7 wherein the detailed monitoring comprises storing physiological signal data upon detecting an event corresponding to one of the first event category and the second event category and further comprising:

storing a priority for each of the first event category and the second event category;

comparing the priority of one of the first and the second event categories corresponding to the detected event and the priority of the other of the first and the second event categories, and if the priority of the one of the first and the second event categories corresponding to the detected event is higher than the priority of the other of the first and the second event categories, overwriting previously stored physiological signal data corresponding to a previously detected event with physiological data corresponding to the detected event, the previously detected event corresponding to the other of the first and the second event categories.

9. The method of claim 1 wherein the detailed monitoring comprises storing a detection threshold for each of the plurality of the first physiological event types.

10. The method of claim 1 wherein the detailed monitoring comprises storing physiological signal data.

11. The method of claim 10 wherein the physiological signal data includes a snapshot of the first physiological signal.

12. The method of claim 11 wherein the detailed monitoring further comprises:

determining a severity index for each of a plurality of previously stored events corresponding to the other of the first and the second event categories;

determining one of the plurality of previously stored events having a lowest severity index; and overwriting the one of the previously stored events having the lowest severity index with the physiological data corresponding to the detected event.

13. The method of claim 1 further comprising:

storing a third threshold, determining if the third threshold has been met in response to the first physiological signal after detailed monitoring has been enabled, and disabling detailed monitoring in response to the third threshold being met.

14. A non-transitory computer-readable medium for storing a set of instructions, which when implemented in an implantable medical device, cause the device to:

store a first threshold corresponding to detecting a first physiological event;

sense a first physiological signal corresponding to the first physiological event;

detect a plurality of the first physiological events in response to the first physiological signal and the first threshold;

store a second threshold different than the first threshold;

determine, in response to detecting at least one of the plurality of the first physiological events, if the second threshold has been met; and enable detailed monitoring of next ones of the detected plurality of the first physiological events in response to the second threshold being met.

15. The computer-readable medium of claim 14 wherein the first physiological event corresponds to a first event category comprising a plurality of first physiological event types, and the detailed monitoring comprises monitoring the plurality of the first physiological event types.

16. The computer-readable medium of claim 15 wherein the detailed monitoring further comprises:

storing physiological signal data in memory in response to detecting an event;

storing a priority for each of the plurality of the first physiological event types, comparing the priority of one of the plurality of the first physiological event types corresponding to the detected event and the priority of an other of the plurality of the first physiological event types, and if the priority of the one of the plurality of the first physiological event types corresponding to the detected event is higher than the priority of the other of the plurality of the first physiological event types, overwriting previously stored physiological signal data corresponding to a previously detected event with the physiological signal data corresponding to the detected event, the previously detected event corresponding to the other of the plurality of the first physiological event types.

17. The computer-readable medium of claim 15 further comprising instructions that cause the system to:
store a third threshold corresponding to detecting a second physiological event;
sense a second physiological signal corresponding to the second physiological event, the second physiological event corresponding to a second event category comprising a plurality of second physiological event types;
detect a plurality of the second physiological events in response to the second physiological signal and the third threshold;
store a fourth threshold different than the third threshold;
determine, in response to detecting at least one of the plurality of the second physiological events, if the fourth threshold has been met; and
enable detailed monitoring of next ones of the detected plurality of the second physiological events in response to the fourth threshold being met.

18. The computer-readable medium of claim 17 wherein the detailed monitoring comprises storing physiological signal data upon detecting an event corresponding to one of the first physiological event category and the second physiological event category and further comprising instructions that cause the system to:
store a priority for each of the first physiological event category and the second physiological event category;
compare the priority of one of the first and the second event categories corresponding to the detected event and the priority of the other of the first and the second event categories, and
if the priority of the one of the first and the second event categories corresponding to the detected event is higher than the priority of the other of the first and the second event categories, overwrite previously stored physiological signal data corresponding to a previously detected event with physiological signal data corresponding to the detected event, the previously detected event corresponding to the other of the first and the second event categories.

19. The computer-readable medium of claim 17 wherein the detailed monitoring further comprises:
determining a severity index for the detected event;
comparing the severity index for the detected event to a severity index of a previously stored event of the same event type;
if the severity index for the detected event corresponds to a more severe event than the previously stored event, determining the least severe of a plurality of previously stored events of the same event type; and
overwriting the least severe of the plurality of the previously stored events with the physiological data corresponding to the detected event.

20. The computer-readable medium of claim 18 wherein the detailed monitoring further comprises:
determining a severity index for each of a plurality of previously stored events corresponding to the other of the first and the second event categories;
determining one of the plurality of previously stored events having a lowest severity index; and
overwriting the one of the previously stored events having the lowest severity index with the physiological data corresponding to the detected event.

21. The computer-readable medium of claim 15 wherein the detailed monitoring comprises storing a detection threshold for each of the plurality of first physiological event types.

22. The computer-readable medium of claim 15 wherein monitoring the plurality of the first physiological event types comprises discriminating between the plurality of the first physiological event types in response to the first physiological signal.

23. The computer-readable medium of claim 15 wherein the detailed monitoring further comprises enabling sensing of a second physiological signal and wherein the monitoring the plurality of the first physiological event types includes detecting at least one of the plurality of the first physiological event types in response to the second physiological signal.

24. The computer-readable medium of claim 14 wherein the detailed monitoring comprises storing physiological signal data.

25. The computer-readable medium of claim 24 wherein the physiological signal data includes a snapshot of the first physiological signal.

26. The computer-readable medium of claim 14 further comprising instructions that cause the system to:
store a third threshold,
determine if the third threshold has been met in response to the first physiological signal after detailed monitoring has been enabled, and
disable detailed monitoring in response to the third threshold being met.

27. An implantable medical device, comprising:
a first physiological sensor for sensing a first physiological signal corresponding to a first physiological event;
a detection module for detecting a plurality of the first physiological events in response to the first physiological signal and a first threshold;
a control module configured to determine, in response to the detection module detecting at least one of the plurality of the first physiological events, if a second threshold has been met, the second threshold being different than the first threshold, and in response to the second threshold being met enable detailed monitoring of next ones of the detected plurality of the first physiological events.

28. The device of claim 27 wherein the first physiological event corresponds to a first event category comprising a plurality of first physiological event types, and the detailed monitoring comprises monitoring the plurality of the first physiological event types.

29. The device of claim 28 further comprising a memory for storing a priority for each of the plurality of the first physiological event types and wherein the detailed monitoring comprises storing physiological signal data in the memory in response to detecting an event corresponding to the first event category;
wherein the control module being further configured to compare the priority of one of the plurality of the first physiological event types corresponding to the detected event and the priority of an other of the plurality of the first physiological event types, and
if the priority of the one of the plurality of the first physiological event types corresponding to the detected event is higher than the priority of the other of the plurality of the first physiological event types, overwriting previously stored physiological signal data corresponding to a previously detected event with the physiological signal data corresponding to the detected event, the previously detected event corresponding to the other of the plurality of the first physiological event types.

30. The device of claim 29 wherein the control module being further configured to determine a severity index for the detected event, compare the severity index for the detected event to a severity index of a previously stored event of the same event type, and if the severity index for the detected event corresponds to a more severe event than the previously stored event, determine the least severe of a plurality of previously stored events of the same event type and overwrite the least severe of the plurality of the previously stored events with the physiological data corresponding to the detected event.

31. The device of claim 28 further comprising:
a second physiological sensor for sensing a second physiological signal corresponding to a second physiological event, the second physiological event corresponding to a second event category comprising a plurality of second physiological event types;
wherein the detection module being configured to detect a plurality of the second physiological events in response to the second physiological signal and a third threshold; and
wherein the control module being configured to determine, in response to the detection module detecting at least one of the plurality of the second physiological events, if a fourth threshold has been met and in response to the fourth threshold being met enable detailed monitoring of next ones of the detected plurality of the second physiological events.

32. The device of claim 31 further comprising a memory for storing a priority of each of the first event category and the second event category and
wherein the memory includes a portion allocated for storing physiological data and the detailed monitoring includes storing physiological signal data in the memory portion upon detecting an event;
wherein the control module being configured to compare the priority of one of the first and the second event categories corresponding to the detected event and the priority of the other of the first and the second event categories, and if the priority of the one of the first and the second event categories corresponding to the detected event is higher than the priority of the other of the first and the second event categories, overwrite previously stored physiological signal data corresponding to a previously detected event with the physiological signal data corresponding to the detected event, the previously detected event corresponding to the other of the first and the second event categories.

33. The device of claim 32 wherein the control module being further configured to determine a severity index for each of a plurality of previously stored events corresponding to the other of the first and the second event categories, determine one of the plurality of previously stored events having a lowest severity index, and overwrite the one of the previously stored events having the lowest severity index with the physiological data corresponding to the detected event.

34. The device of claim 28 wherein the detailed monitoring comprises storing a detection threshold for each of the plurality of the first physiological event types.

35. The device of claim 28 wherein monitoring the plurality of the first physiological event types comprises discriminating between the plurality of the first physiological event types in response to the first physiological signal.

36. The device of claim 28 further comprising a second physiological sensor for sensing a second physiological signal and wherein the detailed monitoring comprises sensing of the second physiological signal and detecting at least one of the plurality of the first physiological event types in response to the second physiological signal.

37. The device of claim 27 further comprising a memory and wherein the detailed monitoring comprises storing physiological signal data in the memory.

38. The device of claim 37 wherein the physiological signal data includes a snapshot of the first physiological signal.

39. The device of claim 27 wherein the control module being further configure to determine if a third threshold has been met in response to the first physiological signal after detailed monitoring has been enabled and disable detailed monitoring in response to the third threshold being met.

* * * * *